(12) United States Patent
Kieser et al.

(10) Patent No.: US 10,646,304 B2
(45) Date of Patent: May 12, 2020

(54) OPTICAL IMAGE VERTEBRAL IMPLANT CAGE AND READING SYSTEM THERFOR

(71) Applicants: Brian Kieser, San Antonio, TX (US); Thomas Zink, San Antonio, TX (US); Nicholas M. Cordaro, Vista, CA (US); Christopher Elkins, San Antonio, TX (US)

(72) Inventors: Brian Kieser, San Antonio, TX (US); Thomas Zink, San Antonio, TX (US); Nicholas M. Cordaro, Vista, CA (US); Christopher Elkins, San Antonio, TX (US)

(*) Notice: Subject to any disclaimer, the term of this patent is extended or adjusted under 35 U.S.C. 154(b) by 289 days.

(21) Appl. No.: 15/806,710

(22) Filed: Nov. 8, 2017

(65) Prior Publication Data

US 2018/0078386 A1 Mar. 22, 2018

Related U.S. Application Data

(63) Continuation-in-part of application No. 14/456,665, filed on Aug. 11, 2014, now Pat. No. 9,943,378, and
(Continued)

(51) Int. Cl.
*A61B 90/90* (2016.01)
*A61F 2/30* (2006.01)
(Continued)

(52) U.S. Cl.
CPC .......... *A61B 90/90* (2016.02); *A61B 17/7004* (2013.01); *A61B 17/80* (2013.01); *A61B 90/39* (2016.02); *A61F 2/30771* (2013.01); *A61F 2/30942* (2013.01); *A61F 2/447* (2013.01); *A61F 2/4455* (2013.01); *A61F 2/4465* (2013.01); *B33Y 80/00* (2014.12); *G06K 7/1099* (2013.01); *G06K 19/06* (2013.01); *G06K 19/06037* (2013.01); *A61B 5/062* (2013.01);
(Continued)

(58) Field of Classification Search
CPC .................................................... A61B 90/90
See application file for complete search history.

(56) References Cited

U.S. PATENT DOCUMENTS 8,136,728 B2 * 3/2012 Turner ...................... A61L 2/07
235/385
2013/0053680 A1 * 2/2013 Frey ......................... A61B 6/12
600/411

* cited by examiner

*Primary Examiner* — Andrew Yang
(74) *Attorney, Agent, or Firm* — Brennan, Manna & Diamond, LLC

(57) ABSTRACT

An implant containing a structurally encoded region, the implant comprising an implant body defining adjacent first and second encoded regions, the first encoded region comprising a first series of shaped inclusions in a first pattern of relatively differing opacity figures, and the second encoded region comprising a second series of shaped inclusions in a second pattern of relatively differing opacity figures, the first and second encoded regions being disposed such that, when the first encoded region and second encoded regions are viewed by reading illumination from a position wherein the first pattern and second pattern overlap, a third pattern is revealed by the reading illumination, the third pattern being different than the first and second patterns, and comprising shape or surface characteristics representing structurally encoded data. The invention further comprises systems and methods of manufacturing, using and reading the same.

14 Claims, 10 Drawing Sheets

Related U.S. Application Data a continuation-in-part of application No. 15/243,036, filed on Aug. 22, 2016, which is a continuation-in-part of application No. 14/823,234, filed on Aug. 11, 2015, now Pat. No. 9,424,503, application No. 15/806,710, which is a continuation-in-part of application No. 15/403,063, filed on Jan. 10, 2017, now Pat. No. 10,152,661, which is a continuation-in-part of application No. 15/243,036, filed on Aug. 22, 2016, which is a continuation-in-part of application No. 14/823,234, filed on Aug. 11, 2015, now Pat. No. 9,424,503.

(60) Provisional application No. 62/419,364, filed on Nov. 8, 2016, provisional application No. 62/419,341, filed on Nov. 8, 2016, provisional application No. 62/419,353, filed on Nov. 8, 2016, provisional application No. 62/419,373, filed on Nov. 8, 2016, provisional application No. 61/938,475, filed on Feb. 11, 2014, provisional application No. 62/035,875, filed on Aug. 11, 2014, provisional application No. 62/035,875, filed on Aug. 11, 2014.

(51) Int. Cl.
*A61F 2/44* (2006.01)
*B33Y 80/00* (2015.01)
*G06K 7/10* (2006.01)
*A61B 17/70* (2006.01)
*A61B 90/00* (2016.01)
*G06K 19/06* (2006.01)
*A61B 17/80* (2006.01)
*A61B 5/06* (2006.01)
*A61B 6/12* (2006.01)
*A61B 17/00* (2006.01)
*B29L 31/00* (2006.01)
*A61B 8/08* (2006.01)

(52) U.S. Cl.
CPC ............... *A61B 5/064* (2013.01); *A61B 6/12* (2013.01); *A61B 8/0841* (2013.01); *A61B 2017/00526* (2013.01); *A61B 2090/3966* (2016.02); *A61F 2002/3008* (2013.01); *A61F 2002/3067* (2013.01); *A61F 2002/3071* (2013.01); *A61F 2002/30617* (2013.01); *A61F 2002/30711* (2013.01); *A61F 2002/30714* (2013.01); *A61F 2002/30774* (2013.01); *A61F 2002/30784* (2013.01); *A61F 2002/30828* (2013.01); *A61F 2002/30892* (2013.01); *A61F 2002/30904* (2013.01); *A61F 2002/4475* (2013.01); *B29K 2995/0056* (2013.01); *B29L 2031/7532* (2013.01); *G06K 2019/06253* (2013.01); *G06K 2019/06271* (2013.01)

OPTICAL IMAGE VERTEBRAL IMPLANT CAGE AND READING SYSTEM THERFOR

RELATED APPLICATION DATA

This application incorporates by reference all of the following in their entirety: U.S. Provisional Application No. 61/938,475, filed Feb. 11, 2014 and U.S. patent application Ser. Nos. 14/302,133, 14/302,171 (now U.S. Pat. No. 9,101,321) and Ser. No. 14/302,197, all filed Jun. 11, 2014, U.S. patent application Ser. No. 14/456,665, filed Aug. 11, 2014 and U.S. Provisional Application No. 62/035,875, filed Aug. 11, 2014, U.S. patent application Ser. No. 14/823,234, filed Aug. 11, 2015, (now U.S. Pat. No. 9,424,503), U.S. patent application Ser. No. 14/822,613, filed Aug. 10, 2015 (now U.S. Pat. No. 9,414,891), and U.S. Provisional Application No. 62/204,233, filed Aug. 12, 2015, and U.S. patent application Ser. No. 15/235,914, filed Aug. 12, 2016, U.S. Provisional Application No. 62/419,341 filed Nov. 8, 2016 entitled Elongate Implant Containing a Structurally Encoded Pin, Carrier and Reading System and U.S. Provisional Application No. 62/419,364, filed Nov. 8, 2016 entitled Optical Image Vertebral Implant Cage and Reading System Therefor, all of which are hereby incorporated by reference in their entirety.

CROSS-REFERENCE

This application claims priority from U.S. Provisional Application Nos. 62/419,364, 62/419,341, 62/419,353 and 62/419,373, all of which were filed on Nov. 8, 2016. This application is also a continuation in part of: (i) U.S. patent application Ser. No. 14/456,665, filed on Aug. 11, 2014, which claims priority to Provisional Patent Application Ser. No. 61/938,475 filed on Feb. 11, 2014; (ii) U.S. patent application Ser. No. 15/243,036, filed on Aug. 22, 2016, which is a continuation of U.S. patent application Ser. No. 14/823,234, filed on Aug. 11, 2015, (now U.S. Pat. No. 9,424,503), which claims the priority benefit of U.S. Provisional Application No. 62/035,875, filed Aug. 11, 2014; and (iii) U.S. patent application Ser. No. 15/403,063, filed on Jan. 10, 2017, which is a continuation of U.S. patent application Ser. No. 15/243,036, filed Aug. 22, 2016, which is a continuation of U.S. patent application Ser. No. 14/823,234, filed on Aug. 11, 2015, (now U.S. Pat. No. 9,424,503), which claims the priority benefit of U.S. Provisional Application No. 62/035,875, filed Aug. 11, 2014.

FIELD OF THE INVENTION

The present invention relates to implants comprising at least two adjacent coding regions each comprising a pattern that may be oriented so as to generate a third pattern viewable from inside or outside of a body, and methods of manufacturing and reading the implants.

BACKGROUND OF THE INVENTION

By way of background, a number of medical conditions such as compression of spinal cord nerve roots, degenerative disc disease, tumor, and trauma can cause severe back pain. Intervertebral fusion is one surgical method of alleviating back pain. In intervertebral fusion, two adjacent vertebral bodies are fused together by removing the affected intervertebral disc and inserting an implant that would allow for bone to grow between the two vertebral bodies to bridge the gap left by the disc removal. Another surgical method of relieving back pain is by corpectomy. In corpectomy, a diseased or damaged vertebral body along with the adjoining intervertebral discs are removed and replaced by a spinal implant that would allow for bone to grow between the closest two vertebral bodies to bridge the gap left by the spinal tissue removal.

A number of different implant materials and implant designs have been used for interbody fusion and for vertebral body replacement with varying success. Current implant materials used include metals, radiolucent materials including plastics, elastic and polymeric materials, ceramic, and allografts. Current implant designs vary from threaded cylindrical implants to rectangular cages with teeth-like protrusions.

Medical implant devices used in surgical procedures, such as those described above, can be associated with particular information to guide medical professionals before and after the surgical procedure. Each implant device carries a wealth of information that is valuable to the patient, the implant manufacturer, medical researchers, healthcare professionals, and medical facilities. However, the information, which may include the implant manufacturer and manufacturer's lot number, the date and location of surgical implantation, the responsible surgeon, any medical notes, photographs, or diagrams relating to the implant, surgery, or condition, may not be adequate, properly recorded, or readily accessible for beneficial use by a healthcare professional, implant manufacturer, or medical researcher after implantation. Problems relating to poor implant records can lead to unnecessary delay or even medical error by healthcare professionals. Moreover, there are many different implant identification methods currently in place instead of a common system to allow manufacturers, distributors, and healthcare facilities and professionals to effectively track, identify, and manage implant devices and medical device recalls. The U.S. Food and Drug Administration recently announced a program focusing on requirements for unique device identifiers for every medical implant device to address the need for a more robust implant device identification system, the details of which are incorporated by reference herein: www.fda.gov/udi as of the filing date.

In imaging implanted devices post implantation, it is oftentimes desirable to be able to retrieve encoded data and images from the structure of the implanted device itself, and to do so in such a way as to maintain the confidentiality and security of the encoded information.

SUMMARY OF THE INVENTION

The following presents a simplified summary in order to provide a basic understanding of some aspects of the disclosed invention. This summary is not an extensive overview, and it is not intended to identify key/critical elements or to delineate the scope thereof. Its sole purpose is to present some concepts in a simplified form as a prelude to the more detailed description that is presented later.

The present invention includes a functional implant body embodying at least two coding regions, the coding regions each comprising relatively radiopaque sub-regions of predetermined perceptible shape and relatively radio-translucent sub-regions of predetermined perceptible shape. The relatively radiopaque sub-regions and relatively radio-translucent sub-regions of each encoded region are adapted to be in at least a partially eclipsed disposition with respect to one another when viewed from a position toward a source of radio-illumination, such that at least partial eclipsing of the patterns of the regions causes the formation of perceptible shapes different than such predetermined perceptible shapes (when viewed with the aid of such radio-illumination), which perceptible shapes represent encoded data.

More specifically, the present invention includes an implant containing a structurally encoded region, the implant comprising an implant body defining adjacent first and second encoded regions. The first encoded region comprises a first series of shaped inclusions in a first pattern of relatively different opacity figures, and the second encoded region comprises a second series of shaped inclusions in a second pattern of relatively different opacity figures, the first and second encoded regions being disposed such that, when the first encoded region and second encoded regions are viewed by reading illumination of any imaging modality from a position wherein the first pattern and second pattern overlap, a third pattern is revealed by the reading illumination. The third pattern being different than the first and second patterns, and comprising shape or surface characteristics representing structurally encoded data.

The first pattern may comprise a pattern of relatively lesser or greater opacity than the surrounding implant body material and, likewise, the second pattern may comprise a pattern of relatively lesser or greater opacity than the surrounding implant body material.

As used herein, the inclusions may be free space or materials of differing opacity or radio-translucence than the surrounding implant body material into which the inclusions are formed or otherwise extend, such that the third pattern may still be revealed by the reading illumination by viewing the two or more eclipsed patterns by virtue of the difference in the opacity or radio-translucence of the constituent patterned material collectively eclipsed. It will be understood that the encoded regions may be created from any combination of inclusion materials of greater light- or radio-translucence or free space to render the constituent two or more patterns eclipsed into a visible third pattern, as described by the examples contained herein.

As will be appreciated from the detailed description and associated figures, the first pattern may comprise a first series of geometric figures and the second pattern may comprise a second series of geometric figures that, when partially overlapped with the first series of geometric figures, will form a third pattern comprising a third series of geometric figures that are different than the first and second geometric figures. As may be appreciated further from the detailed description and drawings, the present invention may be expanded to the use of more than two eclipsing patterns to form the resultant pattern. It should be further appreciated that other encoding symbolism, such as letters, numerals or other indicia representative of the encoded information, can also be used to form the resultant pattern without affecting the overall concept of the present invention.

The implant may be manufactured so that it has an outer surface, and wherein the first series of shaped inclusions and the second (or more) series of shaped inclusions are positioned on the outer surface. For instance, the first and/or second (or more) series of shaped inclusions may comprise a series of grooves in the outer surface so that the third pattern may still be revealed by the reading illumination.

Alternatively, as may be appreciated from the detailed description and associated figures, the first series of shaped inclusions may be positioned on the outer surface and the second (or more) series of shaped inclusions may be beneath the outer surface, while still allowing the third pattern to be revealed by the reading illumination where the implant body is sufficiently translucent to the reading illumination to permit the third pattern to be revealed by the eclipsing first and second series of shaped inclusions.

In still another variation of the present invention, the first and second (or more) series of shaped inclusions both/all may be beneath the outer surface yet the implant material is still sufficiently translucent to the reading illumination to permit the third pattern to be revealed by the eclipsing of said first and second shaped inclusion patterns. In this manner, the encoding remains hidden partially or wholly from plain view, but may be revealed by the reading illumination.

In specific embodiments pertaining to vertebral implants, the present invention may include a vertebral implant comprising an interbody cage, and wherein the first encoded region comprises an upper surface of the interbody cage, and the first series of shaped inclusions comprises a series of notches in the upper surface, wherein the second encoded region comprises a lower surface of the interbody cage, and the second series of shaped inclusions comprises a series of notches in the lower surface.

In another vertebral implant embodiment, the vertebral implant comprises an interbody cage having a graft window, and wherein the first encoded region comprises the first inner graft window surface, and the first series of shaped inclusions comprises a series of notches in the first inner graft window surface, wherein the second encoded region comprises a second inner graft window surface, and the second series of shaped inclusions comprises a series of notches in the second inner graft window surface.

In yet another variation, the vertebral implant may comprise an interbody cage comprising a structurally encoded region comprising an outer surface of the interbody cage having a series of notches in a pattern representing structurally encoded data. The outer surface may further comprise upper and lower contact surfaces comprising anti-migration ridges, wherein the structurally encoded region includes at least one of the upper and lower contact surfaces.

In still another variation, the vertebral implant may contain a structurally encoded region embodied in the implant and comprising an interbody cage having a graft window surface, and wherein the structurally encoded region comprises the graft window surface having a series of notches in a pattern representing structurally encoded data. The structurally encoded region may further include opposing graft window surfaces, each graft window surface having a series of notches in a pattern representing structurally encoded data.

The implant of the present invention may also be of any type or for any medical or therapeutic purpose, and may include, for instance those selected from the group consisting of vertebral implants and the like. Other implants embodying encoded data as described may include pedicle screws, surgical pins, rods, stents and the like. The various implants of the present invention may be manufactured advantageously through additive manufacturing in accordance with known processes and devices.

Additionally, the reading illumination may be that of any appropriate imaging modality such as those selected from the group consisting of visible light, ultraviolet light, x-ray, fluoroscopy, computed tomography, electromagnetic radiation, ultrasound, magnetic resonance imaging, positron emission tomography and neutron imaging, depending upon the nature and thickness of the implant body and the constituent adjacent first and second encoded regions and constituent series of shaped inclusions.

The present invention also includes a method of encoding data onto/into an implant body by forming an implant body bearing at least two coding regions, the coding regions each comprising relatively radiopaque sub-regions of predetermined perceptible shape and relatively radio-translucent sub-regions of predetermined perceptible shape as described above so as to be viewable in at least partially eclipsed disposition to form perceptible shapes as described above, such that those different perceptible shapes represent encoded data. The data may include, for instance, words and/or numerals. Otherwise, the displayed third pattern may be used as a unique symbol such as may be done in a fashion similar to bar codes, or other direct correspondence to a file or database of information, such as through computer pattern recognition. For example, the encoded pattern may be related to a unique numerical identifier corresponding to the associated manufacturer, the implant serial number, installation data, patient, surgeon, or surgical procedure information that may be located in an external healthcare facility or other database.

Another aspect of the present invention is a method of manufacturing an implant containing a structurally encoded region, the method comprising: (a) obtaining data relating to an implant; (b) producing an implant body defining adjacent first and second encoded regions, the first encoded region comprising a first series of shaped inclusions in a first pattern of relatively differing opacity figures, and the second encoded region comprising a second series of shaped inclusions in a second pattern of relatively differing opacity figures, the first and second encoded regions being disposed such that, when the first encoded region and second encoded regions are viewed by reading illumination from a position wherein the first pattern and second pattern wholly or partially overlap, a third pattern is revealed by the reading illumination, the third pattern being different than the first and second patterns, and comprising shape or surface characteristics representing a structurally encoded form of the data.

The method may further include producing the implant by additive manufacturing, wherein the additive manufacturing device is adapted to translate the data into the structurally encoded data in the form of build data for the additive manufacturing device.

Yet another aspect of the present invention is a reading system for reading a plurality of implants, each implant containing a structurally encoded region, comprising: (a) a carrier having a front surface defining a front axis and an upper surface, the upper surface having a plurality of wells arrayed in one or more series; (b) a plurality of implants in respective wells each implant comprising an implant body defining adjacent first and second encoded regions, the first encoded region comprising a first series of shaped inclusions in a first pattern of relatively differing opacity figures, and the second encoded region comprising a second series of shaped inclusions in a second pattern of relatively differing opacity figures, the first and second encoded regions being disposed such that, when the first encoded region and second encoded regions are viewed by reading illumination from a position wherein the first pattern and second pattern overlap, a third pattern is revealed by the reading illumination, the third pattern being different than the first and second patterns, and comprising shape or surface characteristics representing structurally encoded data; and (c) a source of reading illumination directed at the plurality of implants from a position wherein the first pattern and second pattern overlap.

The reading illumination may be selected from the group consisting of visible light, UV light, x-ray, fluoroscopy, computed tomography, or other forms of electromagnetic radiation, ultrasound, and magnetic resonance imaging. The reading system additionally may comprise a means of moving the source of reading illumination with respect to the carrier.

In accordance with further aspects of the present invention, also included is a reading system for reading a plurality of implants each implant containing a structurally encoded region disclosed, comprising generally: (a) a carrier having a front surface defining a front axis and an upper surface, the upper surface having a plurality of wells arrayed in one or more series; (b) a plurality of implants in respective the wells each implant comprising an implant body defining adjacent first and second encoded regions, the first encoded region comprising a first series of shaped inclusions in a first pattern of relatively differing opacity figures, and the second encoded region comprising a second series of shaped inclusions in a second pattern of relatively differing opacity figures, the first and second encoded regions being disposed such that, when the first encoded region and second encoded regions are viewed by reading illumination from a position wherein the first pattern and second pattern overlap, a third pattern is revealed by the reading illumination as described herein, the third pattern being different than the first and second patterns, and comprising shape or surface characteristics representing structurally encoded data; and (c) a source of reading illumination directed at the plurality of implants from a position wherein the first pattern and second pattern overlap.

The reading system may additionally and optionally include a means of moving the source of reading illumination with respect to the carrier. These means may include any means such as manual movement or through the use of mechanical or electromechanical arrangements adapted to move the reading illumination with respect to the carrier, such as along the eclipsing axes described in the drawings.

The present invention further includes a method of reading a plurality of implants each containing a relatively radiopaque encoded portion, comprising: (a) providing a plurality of implants each implant comprising an implant body defining adjacent first and second encoded regions, the first encoded region comprising a first series of shaped inclusions in a first pattern of relatively differing opacity figures, and the second encoded region comprising a second series of shaped inclusions in a second pattern of relatively differing opacity figures, the first and second encoded regions being disposed such that, when the first encoded region and second encoded regions are viewed by reading illumination from a position wherein the first pattern and second pattern overlap, a third pattern is revealed by said reading illumination, the third pattern being different than the first and second patterns, and comprising shape or surface characteristics representing structurally encoded data; and (b) positioning a source of reading illumination directed at the plurality of implants at a position wherein the first pattern and second pattern overlap, so as to read the structurally encoded data from each of the implants. The method additionally may comprise the optional step of decoding the structurally encoded data, and may also include the step of storing the structurally encoded data.

Still another aspect of the present invention is a method of reading, from a single vector, data from a functional implant body bearing at least two coding regions, the coding regions each comprising relatively radiopaque sub-regions of predetermined perceptible shape and relatively radio-translucent sub-regions of predetermined perceptible shape, the implant body relatively radiopaque sub-regions and relatively radio-translucent sub-regions of each encoded region adapted to be in at least a partially eclipsed disposition with respect to one another from a position of a source of radio-illumination, such that at least partial eclipsing causes the formation of perceptible shapes different than such predetermined perceptible shapes when viewed with the aid of such radio-illumination, observing or measuring such different perceptible shapes and translating encoded data therefrom.

The implants of the present invention and the methods relating to same may further incorporate the structurally encoded pin and the applicable methods relating to same as described in U.S. Provisional Application No. 62/419,341, filed Nov. 8, 2016 entitled Elongate Implant Containing a Structurally Encoded Pin, Carrier and Reading System Therefor. Accordingly, the implants of the present invention may include both a structurally encoded pin and encoded inclusion patterns. Further embodiments may also include the use of embedded chips, etc. in the implant in accordance with devices known in the art.

Accordingly, implants of the present invention may have encoded therein some information through the use of the encoded inclusion patterns of the present invention, while other information may be encoded through use of the structurally encoded pins described in the referenced application. Likewise, by combining aspects of both inventions one can use the two (or more) methods together for similar information (either for redundancy or using different methods for reading the information), different information, or some combination of the same or different information, as well as further through the use of embedded chips, etc. for other information within such an encoding scheme.

It will be appreciated that the present invention may be applied to other fields for the inventory management of articles in any industry, such as in the case of articles that may include parts used in manufacturing, such as in the case of automobiles and parts therefor, firearms and parts therefor or jewelry and parts therefor.

In the use of implants it is also beneficial to provide means for organizing, reading, inventorying and using such implants in a therapeutic application, such as in surgical settings and the like. To that end, the present invention may be used to read illumination, such as x-rays and the like, so as to permit all of the encoded implants to be viewed (and decoded) to permit inventory to be tracked and managed in the same manner as the subject implants may be tracked and managed both before and after introduction into the body. The present invention may be applied to other industries, allowing the operator to track anything in any industry with an eclipsing encoded region as described herein and a source of reading illumination, such as x-rays or the like.

To the accomplishment of the foregoing and related ends, certain illustrative aspects are described herein in connection with the following description and the annexed drawings. These aspects are indicative of the various ways in which the principles disclosed herein can be practiced and all aspects and equivalents thereof are intended to be within the scope of the claimed subject matter. Other advantages and novel features will become apparent from the following detailed description when considered in conjunction with the drawings.

BRIEF DESCRIPTION OF THE FIGURES

While the specification concludes with claims particularly pointing out and distinctly claiming the present invention, it is believed that the present invention will be better understood from the following description in conjunction with the accompanying Figures, in which like reference numerals identify like elements, and wherein:

DETAILED DESCRIPTION

Figure 1:
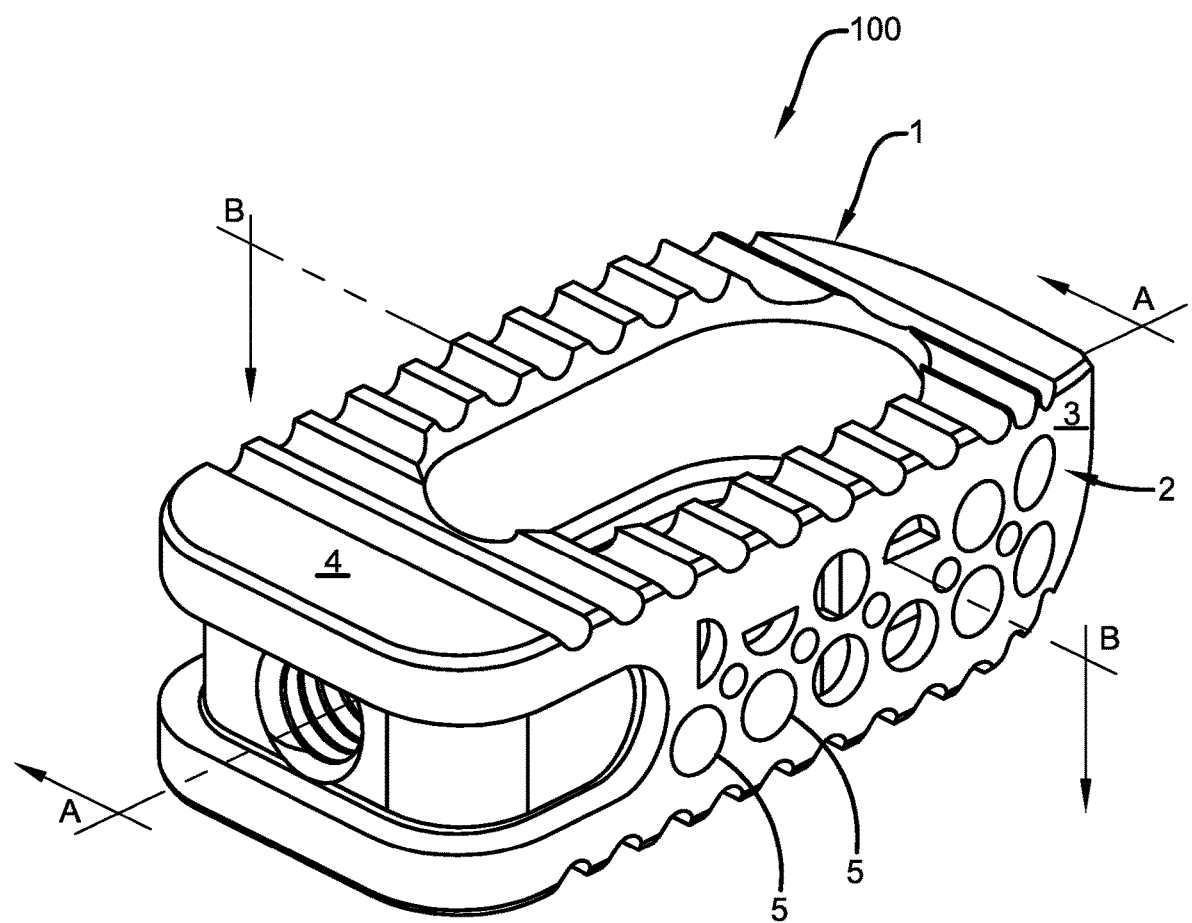
FIG. 1 is an upper perspective view of an implant in accordance with an embodiment of the present invention.

Reference is now made to the drawings, wherein like reference numerals are used to refer to like elements throughout. In the following description, for purposes of explanation, numerous specific details are set forth in order to provide a thorough understanding thereof. It may be evident, however, that the novel embodiments can be practiced without these specific details. In other instances, well known structures and devices are shown in block diagram form in order to facilitate a description thereof. The intention is to cover all modifications, equivalents, and alternatives falling within the spirit and scope of the claimed subject matter. The present invention generally relates to an implant comprising a structurally encoded portion that is readable using a source of reading illumination, such as an x-ray, a system for reading the implant, and methods for manufacturing and reading the same.

Figure 4:
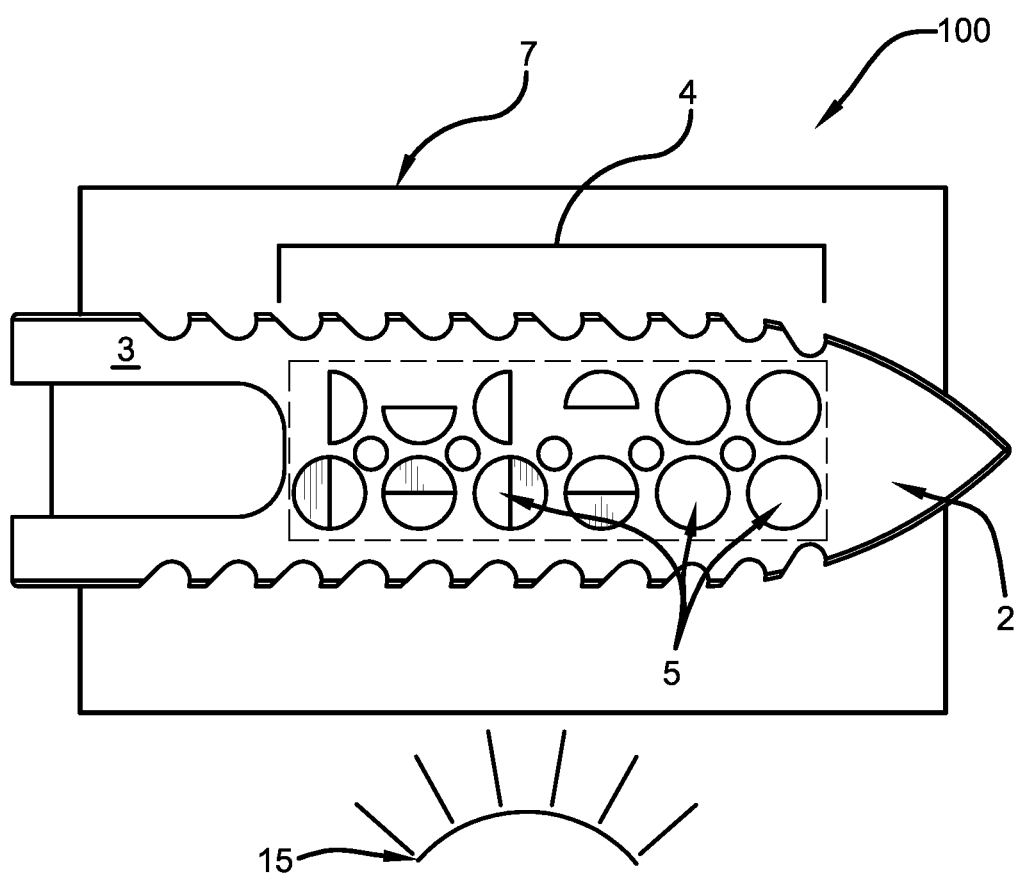
FIG. 4 is a lateral view of the implant of FIG. 1 positioned over an illumination sheet in accordance with the present invention.
Figure 5:
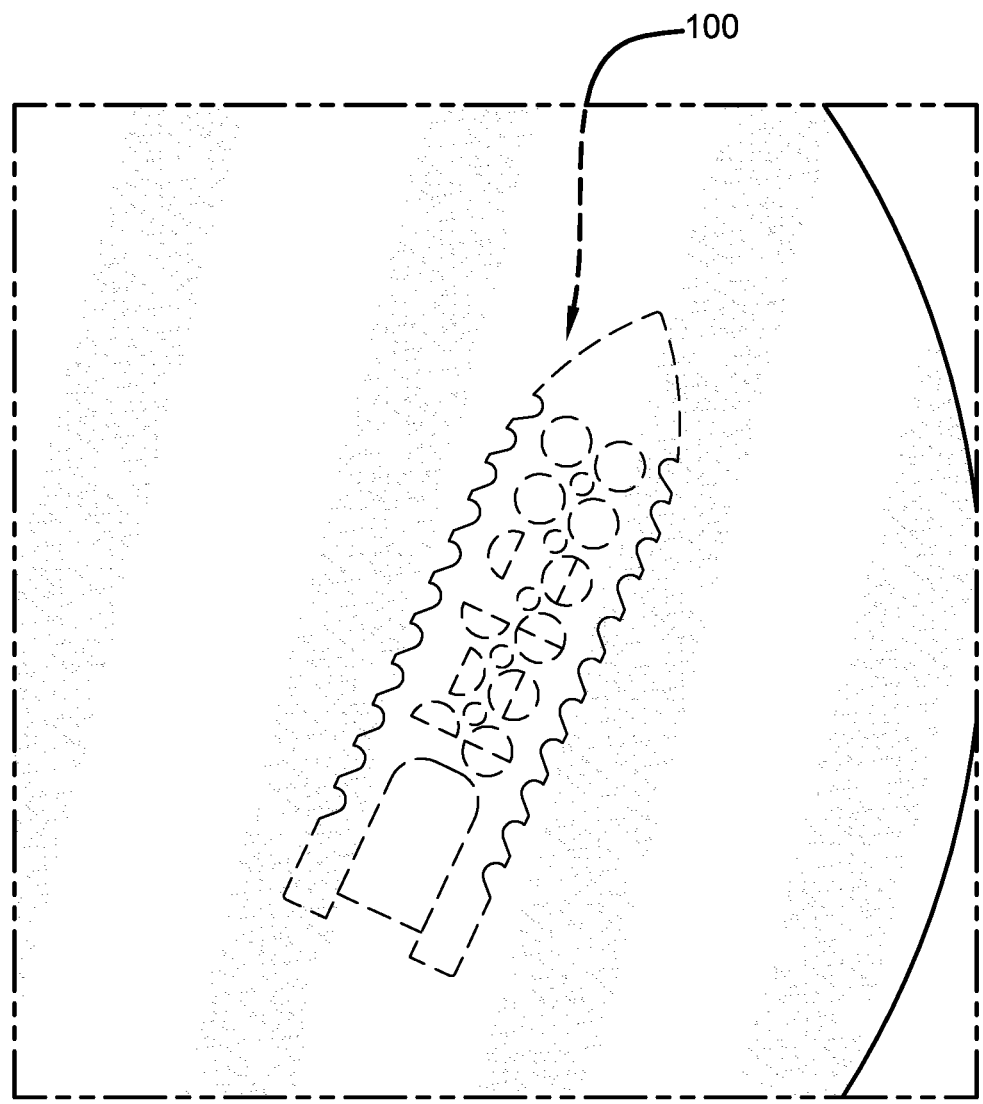
FIG. 5 is a lateral radiographic view of the implant in accordance with an embodiment of the present invention.
Figure 6:
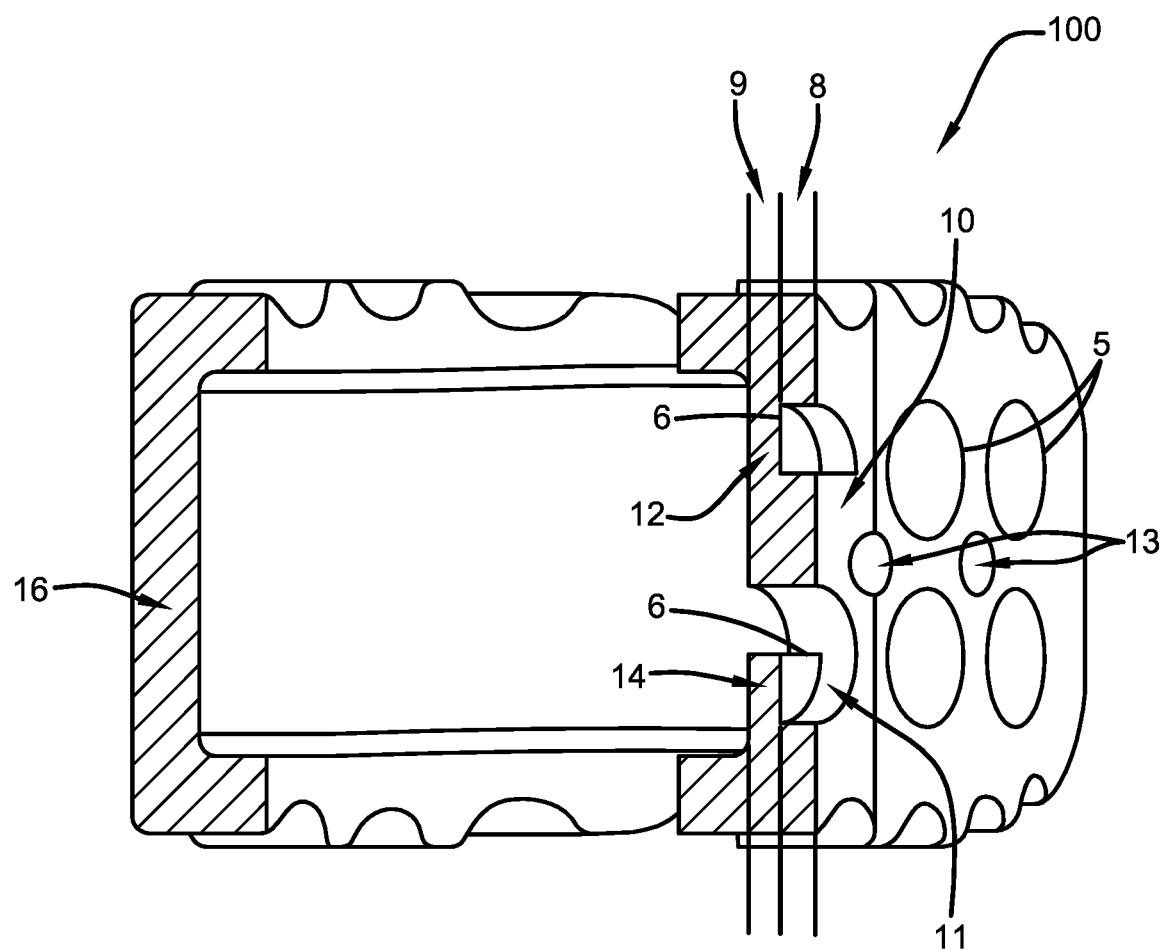
FIG. 6 is a lateral perspective sectioned view taken along line B-B of the implant of FIG. 1 in accordance with the present invention.

FIGS. 1-7 illustrate an implant 100 in accordance with an embodiment of the present invention. The implant 100 comprises an implant body 1 comprising a structurally encoded portion 2. The structurally encoded portion 2 comprises a first encoded region 8 and a second encoded region 9. As illustrated in FIG. 6 the first encoded region 8 and the second encoded region 9 are adjacent to one another. The implant body 1 comprises an outer surface defined by at least one lateral surface 3 and at least one lateral side 3. The structurally encoded portion 2 may be disposed along the outer surface of the implant body 1 and extend into a three-dimensional space within the dimensions of the implant 100 generally beneath lateral surface 3 and generally within lateral side 4.

As can be appreciated from FIG. 3, the first encoded region 8 is generally a region comprised by a first depth below lateral surface 3. The first encoded region 8 of the structurally encoded portion 2 comprises a first series of shaped inclusions 5 located within or beneath the lateral surface 3 of the outer surface of the implant body 1. The first series of shaped inclusions 5 may be generally spatially shaped, such as, but not limited to, circular and semi-circular shapes of differing orientations. The first series of shaped inclusions 5 may also include voids. The first series of shaped inclusions 5 are arranged in a first pattern. The plurality of shapes of the first pattern may comprise figures or shapes of relatively differing opacity.

As can be appreciated from FIG. 2, the second encoded region 9 is generally a region comprised by a second depth below lateral surface 3. The second encoded region 9 of the structurally encoded portion 2 comprises a second series of shaped inclusions 6 located within the lateral surface 3, adjacent to the first series of shaped inclusions 5. The second series of shaped inclusions 6 may also be generally spatially shaped, such as, but not limited to, circular and semi-circular shapes of differing orientations. The second series of shaped inclusions 6 may also include voids. The second series of shaped inclusions 6 are arranged in a second pattern. The plurality of shapes of the second pattern may comprise figures or shapes of relatively differing opacity similar to the plurality of shapes of the first pattern.

As illustrated in FIG. 4, the implant 100 may be placed on an illumination sheet 7. The structurally encoded portion 2 would then be viewable when a source of reading illumination 15, such as, but not limited to, an x-ray, visible light, UV light, fluoroscopy, computed tomography, electromagnetic radiation, ultrasound, magnetic resonance imaging, positron emission tomography and neutron imaging is directed at the implant 100 as described infra.

Figure 2:
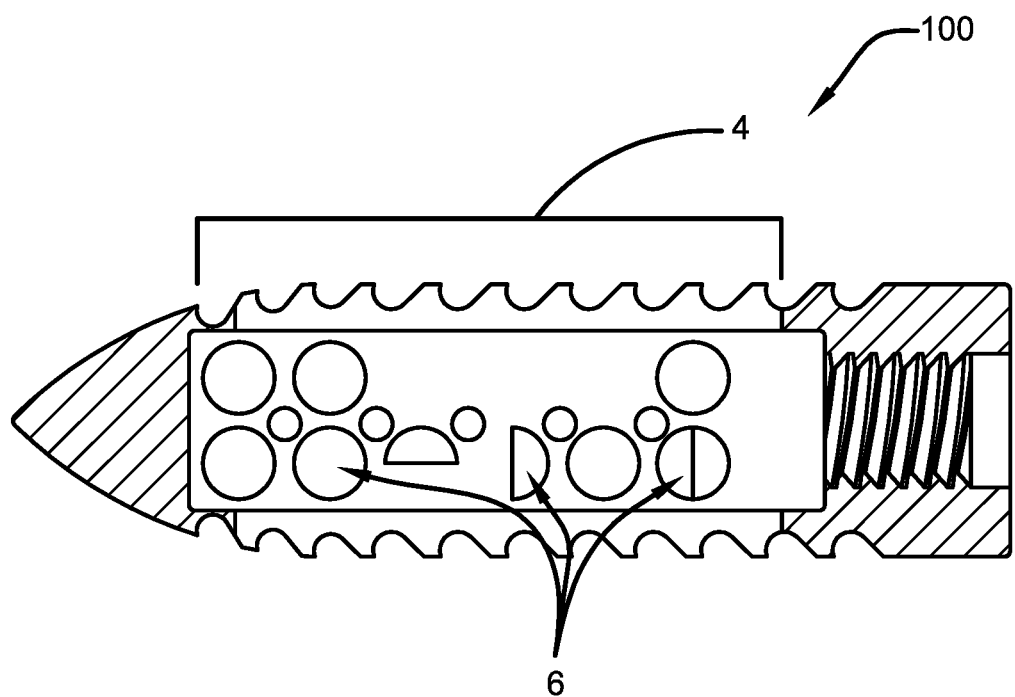
FIG. 2 is a lateral sectioned view taken along line A-A of the implant of FIG. 1 in accordance with the present invention.
Figure 3:
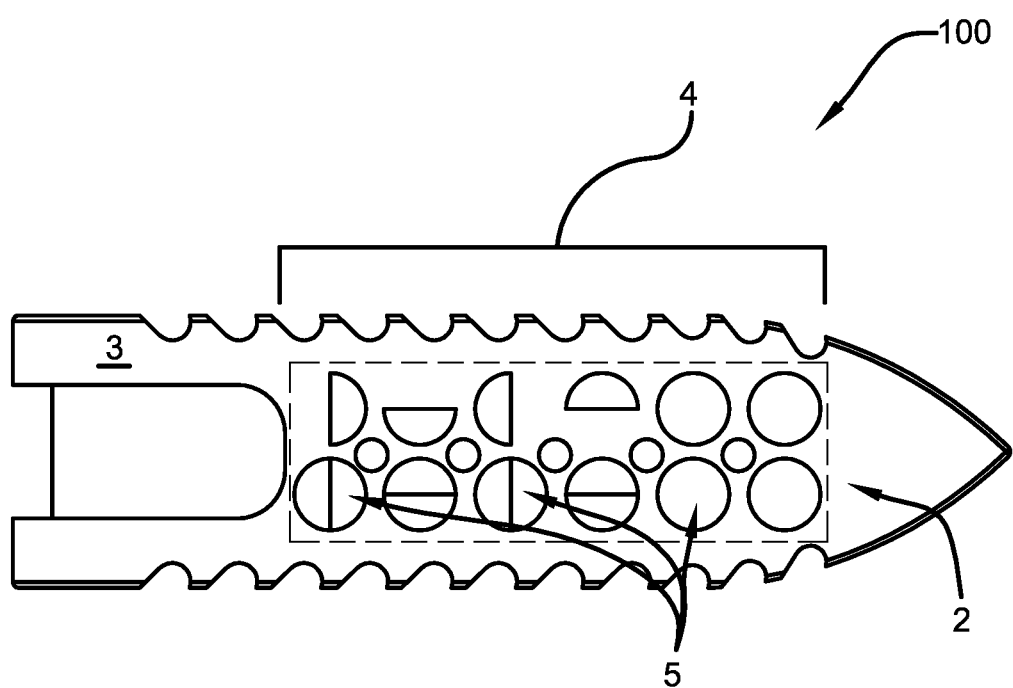
FIG. 3 is a lateral view of the implant of FIG. 1 in accordance with the present invention.

As may be appreciated from FIGS. 2-4, the first and second encoded regions 8 and 9 are disposed such that, when they are viewed by the source of reading illumination 15 from a position wherein the first and second patterns overlap so that the two patterns eclipse one another, a third pattern is revealed by the source of reading illumination 15. The third pattern is created by virtue of the differing collective translucence of the eclipsed shapes of the first and second patterns. The revealed third pattern is different than the first and second patterns, and comprises a plurality of shapes or surface characteristics representing structurally encoded data.

The first pattern may be relatively more opaque, less opaque, or a combination thereof as compared to a portion of the surrounding implant body 1. Similarly, the second pattern may be relatively more opaque, less opaque, or a combination thereof as compared to the surrounding implant body 1. Additionally, the first pattern may be relatively more opaque, less opaque, or a combination thereof as compared to the second pattern.

FIG. 5 illustrates the third pattern revealed by the reading illumination. As may be appreciated from this view, the overlapping first and second patterns each formed of differing shapes and differing translucence, form the third pattern of shapes that differ in shape and brightness as compared to that of the first and second patterns. Accordingly, one can discern that the overlapping first and second patterns form the third pattern that may comprise full circles, semi-circles, or quarter circles, or even no circles of differing brightness, depending upon the nature, orientation and shape of the constituent materials and shapes of the first and second series of shaped inclusions 5 and 6, respectively.

Thus, the encoding concept of the present invention may be applied to the implant 100. In this exemplary embodiment, shapes such as "no moon," "full moon," or "crescent moons" (oriented up, down, left or right with respect to the viewer), etc. are directly carved onto or into the implant body 1 at different depths. Variability may further be increased by placing a crescent moon shape in front a full moon shape. A secondary advantage of the encoding strategy of the present invention is that the same features may be viewed both visually as well as being captured via photo documentation as well as with the x-ray or other illumination source detection. This may be accomplished with any feature type that is viewable without an x-ray or other illumination source detection and that presents no conflicting shapes when viewed via an x-ray. For the current configuration, the structurally encoded data of the implant 100 is visually more discernable when placed on or near the contrasting colored backdrop illumination sheet 7 as shown in FIG. 4. Another benefit of the present invention is that the structurally encoded data is discernable using the x-ray or other illumination detection source whether the implant 100 is located in vivo or ex vivo. For example, before implantation, a visual inspection system of photo comparison may be used. Once inside the body, the x-ray or other illumination detection source is used to view the structurally encoded data.

FIG. 6 illustrates a lateral perspective sectioned view of the implant 100 taken along line B-B of FIG. 1. From this view the eclipsed first encoded region 8 and second encoded region 9 containing the respective first and second series of patterned inclusions 5 and 6 may be appreciated. The first pattern may further comprise a first set of geometric figures locatable within a plurality of apertures within the lateral surface 3. The second pattern may further comprise a second set of geometric figures locatable within the plurality of apertures within the lateral surface 3. The plurality of apertures (or, alternatively differing material inclusions) form the "moon" shapes such as a half-moon shape 10 (i.e., upper void, lower filled) and a full moon shape 11 in first encoded region 8, and a no moon 12 shape (i.e., completely filled) and a half-moon shape 14 (upper void, lower filled) in the second encoded region 9. The third pattern may be further comprised of a third set of geometric figures different from and formed from the combination of the first and second series' geometric figures.

In this example, the plurality of apertures may be approximately between 0.6 mm to 2 mm in diameter to allow for proper feature additive manufacturing. However, the diameter of a given aperture may be larger or smaller than the above range, as the aperture diameter is only dependent on the size of the implant 100. Further, each of the plurality of apertures comprises an upper portion and a lower portion. The first series of geometric figures is located within the upper portion, and the second series of geometric figures is located within the lower portion.

FIG. 6 illustrates an example where the upper portion of one of the plurality of apertures uses an approximately 0.5 mm thick no (or new) moon 12 behind an approximately 0.5 mm thick downward-facing half crescent moon 10. However, the thickness of a given inclusion may be thicker or thinner than the above range, as the thickness is only dependent on the ability of the source of reading illumination to read the patterns. The third pattern formed by the eclipse of these shapes results in a moderately light downward-facing half crescent moon with a relatively dark lower half.

Additionally, the upper portion of an adjacent one of the plurality of apertures uses an approximately 0.5 mm thick downward-facing half crescent moon 14 behind an approximately 0.5 mm thick circular full moon 11. The third pattern formed by the eclipse of these shapes results in a very light downward-facing half crescent moon with a moderately light lower half crescent.

The structurally encoded portion 2 may further comprise a plurality of smaller centralized holes 13. The plurality of smaller centralized holes 13 may be approximately between 0.4 to 1 mm in diameter and contain only a full moon or no moon shapes. The plurality of smaller centralized holes 13 may be used as indicators for error coding and as a code for where to start reading an algorithm or other structurally encoded data coded within the structurally encoded portion 2. The implant body may further comprise a solid back wall 16 approximately 1 mm in thickness opposed to lateral side 4 bearing the encoding so as to avoid distortion from the encoded respective first and second series of shaped inclusions 5 and 6 to provide x-ray opacity behind the formed third pattern of shapes while adding strength to the implant body 1. The implant body 1 may be manufactured as a titanium cage, or from any other biocompatible, radiopaque material.

Additional details of the variations for structurally encoded portion 2 of the implant 1 may include twelve larger apertures that have the have the following approximate dimensions and variations:

Left-facing crescent (½ mm thick)
Downward-facing crescent (½ mm thick)
Right-facing crescent (½ mm thick)
Upward-facing crescent (½ mm thick)
Left-facing crescent with full back plate
Downward-facing crescent with full back plate
Right-facing crescent with full back plate
Upward-facing crescent with full back plate
Thru hole (full moon)
No Hole (no/new moon)
Hole with back plate 16 only (not shown)

The plurality of smaller centralized holes 13 may include five smaller holes each having two variations: present or not present. All variations of the displayed embodiment may be readable with and without x-ray reading illumination. Alternative embodiments may include those where the first and second encoded regions 8 and 9 may be fully located below the outer surface of the implant 100 so as to be readable only through a source of reading illumination 15, such as, but not limited to x-ray, fluoroscopy, computed tomography, electromagnetic radiation, ultrasound, magnetic resonance imaging, positron emission tomography and neutron imaging.

The resulting patterns may be encoded using any correspondent coding system wherein the revealed third pattern shapes differ in shapes and/or brightness and/or orientation within an array so as to stand for or signify a letter, numeral, punctuation or other symbol so that the first and second patterns can be determined and embodied in the implant accordingly to encode the desired data. In other embodiments, the displayed third pattern may be used and stored as a unique symbol such as may be done in a fashion similar to bar codes, or other direct correspondence to a file of information such as through pattern recognition. The encoded pattern may further be associated with a database containing a plurality of records associated with a plurality of implantable devices and a user interface comprising means for displaying information associated with the indicia based on the plurality of records. The encoded pattern may in turn be related to a unique numerical identifier corresponding to the associated manufacturer, serial number, installation data, patient, surgeon, or surgical procedure information that may be located in an external healthcare facility or other database.

Figure 7:
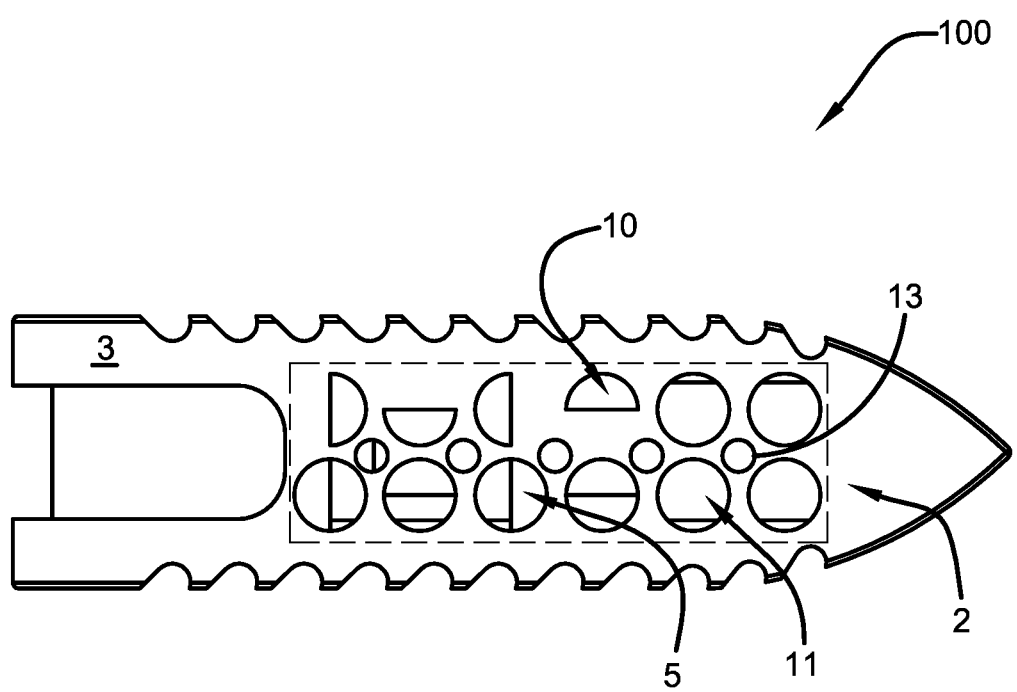
FIG. 7 is a lateral view of the implant in accordance with an embodiment of the present invention.

FIG. 7 illustrates the third pattern formed by the eclipse of different shapes of differing brightness as compared to that of the first and second patterns. From this view one can appreciate the apertures (or, alternatively differing material inclusions) forming the "moon" shapes such as the half-moon shape 10 (i.e., upper void, lower filled) and the full moon shape 11 in first encoded region 8, as well as the other possible third pattern constituent shapes that may be formed through the encoding of the present invention. Using the array of the first and second patterns employing the moon phase shapes as described above, and plurality of smaller centralized holes 13, this embodiment with twelve larger circles and five smaller circles, potentially gives: $12^{11} \times 5^2$ variations or 7,430,083,706,880 variations, all readable via photo documentation and the source of reading illumination 15, such as an x-ray.

The constituent first and second patterns optionally may be formed by areas of different inclusion depth and optionally may include areas of free space or inclusions of materials of greater or lesser translucence to the reading illumination. Using such different depths and/or inclusion fill materials will permit the creation of different shapes or differing degrees of brightness lending additional dimensions to the encoding in the third pattern revealed by the reading illumination.

It will be understood that the present invention may be extended to include embodiments that employ more than two series of shaped inclusions to add further constituent pattern levels, adding to the complexity of the resulting pattern formed through the reading illumination. Such additional series of shaped inclusions and their respective patterns may be employed to add additional complexity and degrees of freedom the encoded data read from the resulting pattern, such as further variations in the resultant shapes in the resulting pattern and their relative apparent brightness.

Figure 8B:
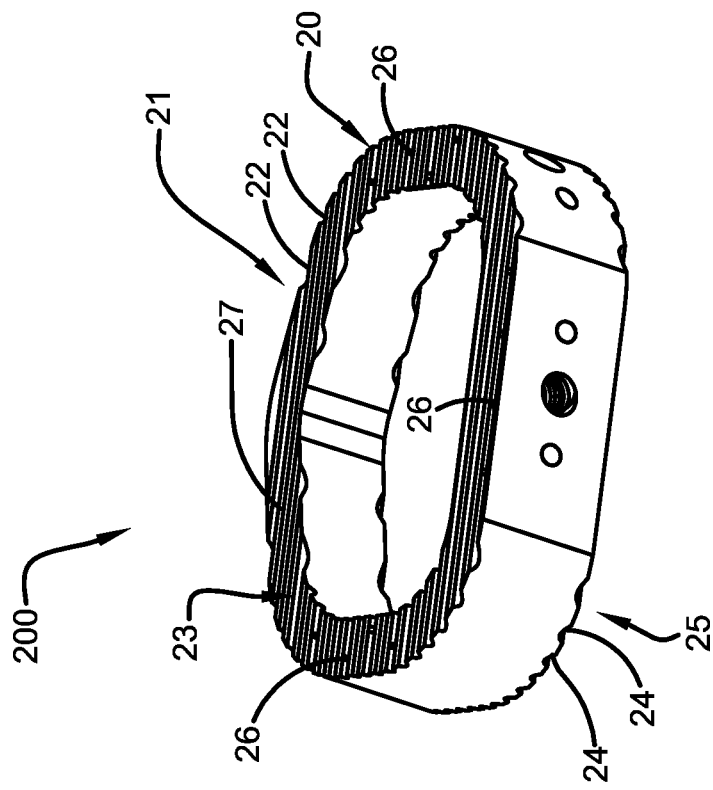
FIG. 8b is an upper perspective view of the vertebral implant in accordance with another embodiment of the present invention.
Figure 8A:
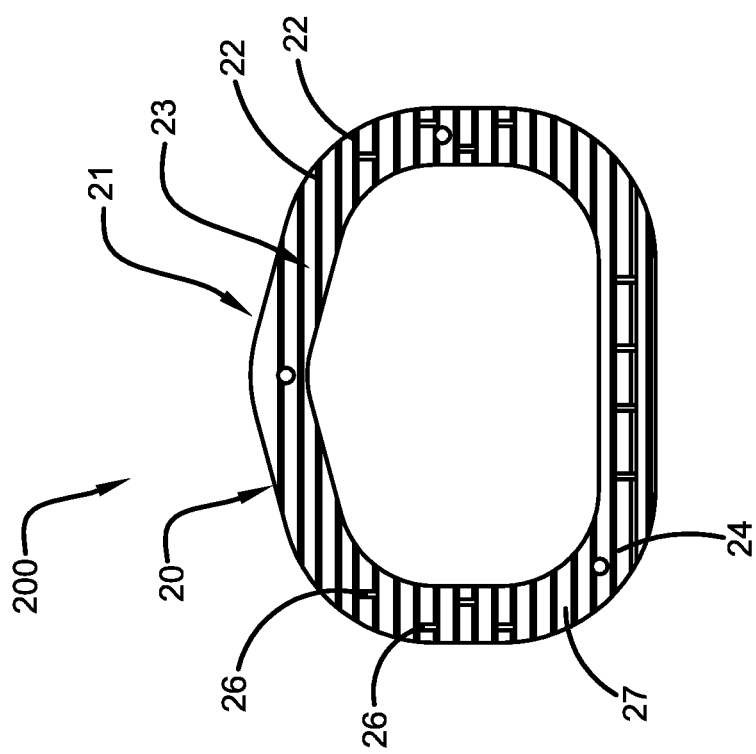
FIG. 8a is a top plan view of a vertebral implant in accordance with another embodiment of the present invention.

FIGS. 8A and 8B illustrate a vertebral implant 200 in accordance with another embodiment of the present invention. The implant 200 comprises an implant body 20 comprising an interbody cage 21. This embodiment demonstrates that the present invention may be adapted for use in PEEK interbody cages. The interbody cage 21 comprises an upper surface 23 and a lower surface 25. The implant body 20 further comprises a structurally encoded portion comprising a first encoded region and a second encoded region. The first encoded region comprises a first series of shaped inclusions such as a first series of notches 22 located within the upper surface arranged in a first pattern. The second encoded region comprises a second series of shaped inclusions such as a second series of notches 24 located within the lower surface arranged in a second pattern. Both the first series of notches 22 and the second series of notches 24 may be arranged in patterns that represent structurally encoded data. The notches 22 and 24 may further comprise other radiopaque inclusions as desired. The implant body 20 may further comprise a plurality of anti-migration elements 27, such as ridges in either or both surfaces. The marks in the form of a plurality of notches 26 (or other radiopaque inclusions) on the upper surface of the implant that interrupt the anti-migration features (i.e., ridges 27, see the same features in FIGS. 1 through 7) as shown can be coded to match the encoded markers that may be pressed into the device in accordance with inventions disclosed in the incorporated references. Such encoding may be accomplished for instance through the use of eclipsing patterns of marks or notches on the underside likewise interrupting the anti-migration features, similar to that described in FIGS. 1 through 7), to reveal a third pattern upon elucidation through reading illumination or through visual inspection or optical inspection, as described herein. These encoded patterns may be used on all types of PEEK interbody cages.

Figure 9:
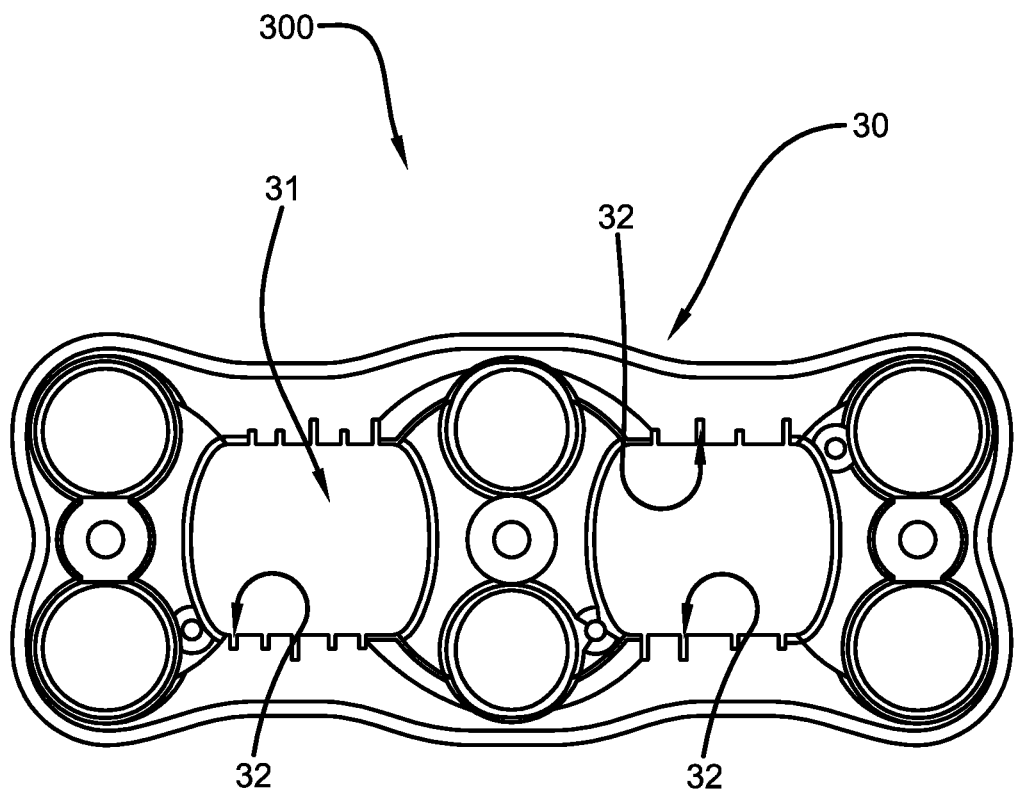
FIG. 9 is a top plan view of a vertebral implant in accordance with another embodiment of the present invention.
Figure 10:
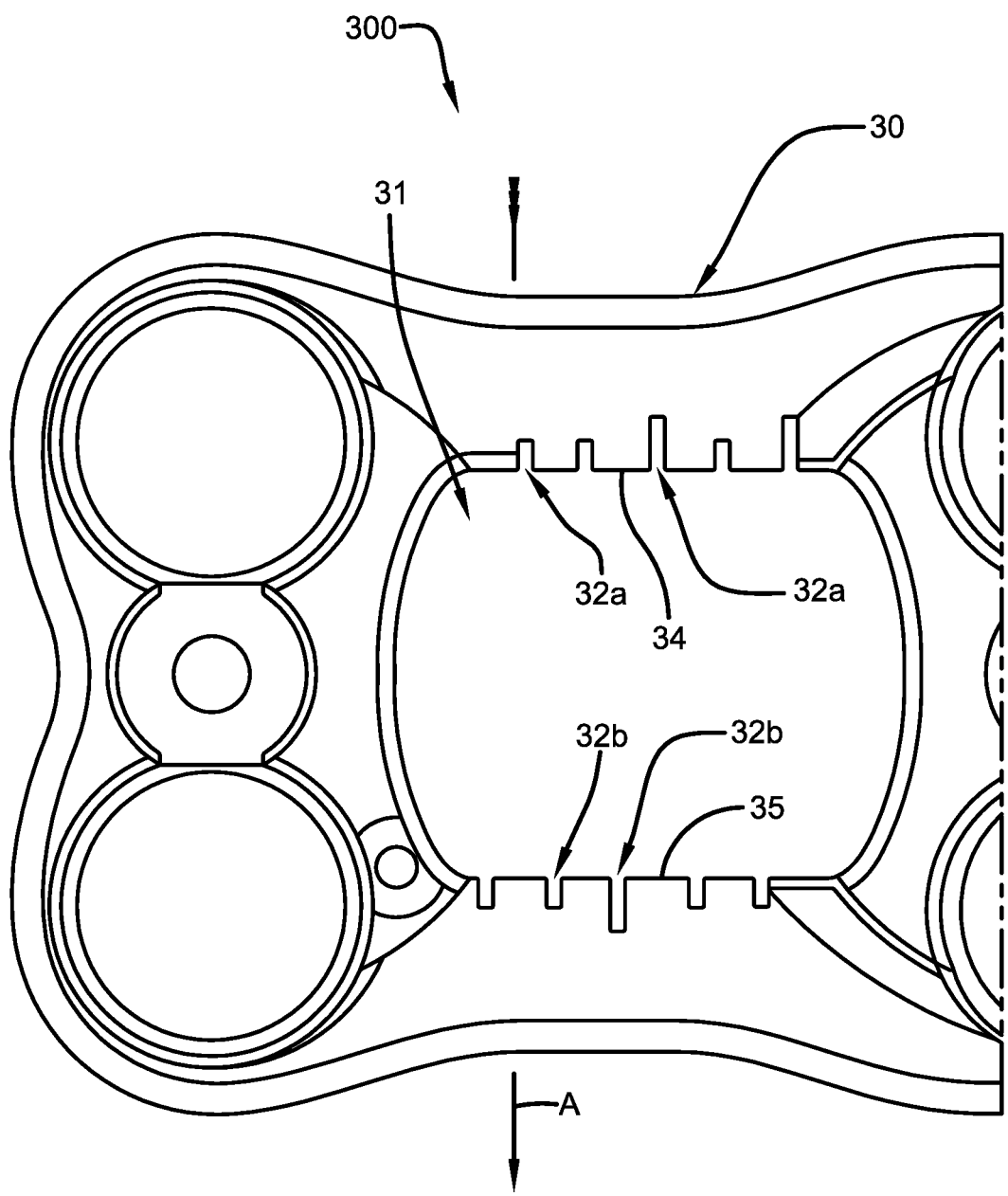
FIG. 10 is a detailed top plan sectioned view of the vertebral implant in accordance with another embodiment of the present invention.

FIGS. 9 and 10 illustrate a vertebral implant 300, such as a PEEK interbody cage, in accordance with another embodiment of the present invention. The vertebral implant 300 comprises an implant body comprising an interbody implant cage 30. The interbody implant cage 30 comprises a graft window 31 comprising a first inner window surface 34 and a second inner window surface 35. The first inner window surface 34 is generally oppositely disposed from the second inner window surface 35. The interbody implant cage 30 further comprises a structurally encoded portion comprising a series of radiopaque inclusions 32. The structurally encoded portion further comprises a first encoded region and a second encoded region. The first encoded region comprises a first series of shaped inclusions such as a first series of notches 32A located within the first inner window surface 34 arranged in a first pattern. The second encoded region comprises a second series of shaped inclusions such as a second series of notches 32B located within the second inner window surface 35 arranged in a second pattern. Both the first series of notches 32A and the second series of notches 32B may be arranged in patterns that represent structurally encoded data. The notches 32A and 32B may be encoded with data, and that are both optically and radiographically visible.

The notches 32A and 32B (or other radiopaque inclusions 32) in this embodiment on the interior surface of the graft window 31 that interrupt the otherwise uniform surfaces (i.e., similar to the notches 26 in FIGS. 8A and 8B) as shown can be coded to match the encoded markers that may be pressed into the device in accordance with inventions disclosed in the incorporated references. Such encoding may be accomplished for instance through the use of eclipsing patterns of marks or notches in other planes within the interbody implant cage 30, similar to that described in FIGS. 1 through 7), to reveal a third pattern upon elucidation through reading illumination or through illumination-aided visual inspection or optical inspection, as described herein.

FIG. 10 illustrates a more detailed view of the PEEK interbody cage 30 having the notches 32, 32A and 32B in the graft window 31 that may be encoded with data, as described above. Additionally, the formation of a third pattern that the notched patterns formed in opposing graft window surfaces 34 and 35 (i.e., notches 32A and 32B, respectively) may be revealed through reading illumination or through illumination-aided visual inspection or optical inspection, viewed along direction A. As such, that the first and second patterns formed by notches 32A and 32B become eclipsed so as to form a reveled third pattern arising from the differential in translucence.

It will be appreciated that the embodiments described in FIGS. 8A-10 may also be used to encode information directly into the notches such that the data may encoded directly and read without the formation of a third pattern as described herein, so that the data may be decoded directly from the notch pattern without the need to eclipse two or more patterns.

The information or data encoded onto or into the implants of the embodiments disclosed in the present invention may be detected, decoded, read, transferred, stored, displayed, or processed according to such methods and devices disclosed in U.S. Pat. No. 8,233,967 or U.S. Patent Application Publication No. 2013/0053680, both of which are incorporated herein by reference.

The implantable devices, such as implants 100, 200, and 300, may be manufactured by first obtaining data relatable to the implant that would be desirable to be encoded. The implants of the present invention may be manufactured using additive manufacturing (AM) techniques, or using a combination of other molding or machining techniques (injection molding, machining, etc.) to produce the subject encoded implants. These additional techniques include without limitation material extrusion, vat photo polymerization, powder bed fusion, material jetting, binder jetting, sheet lamination, and directed energy deposition.

The implantable devices used in accordance with the present invention may be manufactured by conventional methods such as a machining operation using any milling, lathe, or drilling operation to include standard machining and fabrication methods known in the art of manufacturing medical implants.

The present invention thus permits the convenient, accurate and efficient reading of structurally encoded articles such as the implant of the present invention.

A typical embodiment of the structurally encoded implants of the present invention may contain data that is not readily apparent to a viewer of the device structure. Further, encoding of the typical embodiments of the present invention is handled by physical means other than those accomplished through circuitry, electromagnetic or other, within the implant device itself or through a type of internal storage means such as magnetic storage means or the like. Such structurally encoded devices, as disclosed herein and described in relation to the typical and/or preferred embodiments of the present invention allow simplified production, maintenance, and/or operation costs for identification, storage, and/or retrieval of unique implant data while retaining a substantial amount of information with reduced probability for error.

The implant device carrier of the present invention enables better reporting, reviewing, inventorying and analyzing of implant devices to reduce medical error by enabling health care professionals and others to rapidly and precisely identify an implant device and obtain important information concerning the characteristics of the device, principally prior to installation. The present invention enhances analysis of devices on the market by providing a standard and clear way to document device use in electronic health records, clinical information systems, claim data sources, and registries.

It will also be appreciated that the present invention may be applied to similarly prepared articles such as articles that may benefit from structurally encoded structures as in the present invention. Such articles may include parts used in manufacturing, such as in the case of automobiles and parts therefor, firearms and parts therefor or jewelry and parts therefor.

The present invention also includes methods of reading the structurally encoded articles manufactured as described supra, as well as an inventory management system for structurally encoded articles that includes reading the encoded data from the encoded articles and storing the acquired data. The source of reading illumination may be directed at the implants from a position where the first and second patterns overlap to create the third pattern representing structurally encoded data. The data, once read, may be decoded and stored.

Other variations are within the spirit of the present invention. Thus, while the invention is susceptible to various modifications and alternative constructions, a certain illustrated embodiment thereof is shown in the drawings and has been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein. Variations of those preferred embodiments may become apparent to those of ordinary skill in the art upon reading the foregoing description. The inventor expects skilled artisans to employ such variations as appropriate, and the inventor intends for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An implant comprising:
an implant body comprising a structurally encoded portion comprising a first encoded region and a second encoded region adjacent to the first encoded region, wherein the first encoded region comprises a first series of inclusions arranged in a first pattern, the second encoded region comprises a second series of inclusions arranged in a second pattern, and the first and second patterns overlap so as to define a third pattern representing structurally encoded data and further wherein the first pattern is relatively more or less opaque than a portion of the implant body.

2. The implant of claim 1, wherein the first and second patterns each comprise a plurality of shapes.

3. The implant of claim 1, wherein the structurally encoded data is discernable via a source of reading illumination.

4. The implant of claim 1, wherein the second pattern is relatively more or less opaque than a surrounding implant body.

5. The implant of claim 1, wherein the first pattern comprises a first series of geometric figures, the second pattern comprises a second series of geometric figures, and the third pattern comprises a third series of geometric figures different from the first and second series of geometric figures.

6. The implant of claim 1, wherein the implant body further comprises an outer surface, and wherein the first series of inclusions is located within the outer surface.

7. The implant of claim 1, wherein the implant body further comprises an outer surface, and wherein the first series of inclusions comprises a series of grooves in the outer surface.

8. The implant of claim 1, wherein the implant body further comprises an outer surface, and wherein the first and second series of inclusions are located within the outer surface.

9. The implant of claim 1, wherein the implant body further comprises an outer surface, and wherein the first series of inclusions are located within the outer surface and the second series of inclusions are located beneath the outer surface.

10. The implant of claim 1, wherein the implant body comprises an outer surface, and wherein the first and second series of inclusions are located beneath the outer surface.

11. The implant of claim 1, wherein the implant body further comprises an interbody cage comprising an upper surface and a lower surface, and wherein the first series of inclusions comprise a first series of notches in the upper surface and the second series of inclusions comprise a second series of notches in the lower surface.

12. The implant of claim 1, wherein the implant body further comprises an interbody cage comprising a graft window comprising a first inner window surface and a second inner window surface, and wherein the first series of inclusions comprise a first series of notches in the first inner window surface and the second series of inclusions comprise a second series of notches in the second inner window surface.

13. A method of manufacturing an implant, the method comprising:
obtaining data relating to the implant; and
manufacturing an implant comprising a structurally encoded portion comprising a first encoded region and a second encoded region, wherein the first encoded region comprises a first series of inclusions arranged in a first pattern, the second encoded region comprises a second series of inclusions arranged in a second pattern, and the first and second patterns overlap so as to define a third pattern representing structurally encoded data and further wherein the first pattern is relatively more or less opaque than a portion of the implant.

14. The method of claim 13, wherein the implant is manufactured using an additive manufacturing process adapted to translate the data relating to the implant into structurally encoded data, and further wherein the first encoded region is adjacent to second encoded region.

* * * * *